US006174669B1

(12) United States Patent
Hayashizaki et al.

(10) Patent No.: US 6,174,669 B1
(45) Date of Patent: *Jan. 16, 2001

(54) METHOD FOR MAKING FULL-LENGTH CDNA LIBRARIES

(75) Inventors: Yoshihide Hayashizaki; Piero Carninci, both of Ibaragi (JP); Claudio Schneider, Trieste (IT)

(73) Assignee: The Institute of Physical and Chemical Research, Saitama (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/752,540

(22) Filed: Nov. 20, 1996

(30) Foreign Application Priority Data

Mar. 18, 1996 (JP) ........................................................ 8-60459

(51) Int. Cl.$^7$ .............................. C12Q 1/68; C07H 21/04; C07H 21/02
(52) U.S. Cl. .................................. 435/6; 435/7.1; 435/7.5; 435/91.1; 536/23.1; 536/23.5
(58) Field of Search ................................ 435/6, 7.1, 7.5, 435/91.1, 172.3; 536/23.1, 23.5; 935/80

(56) References Cited

U.S. PATENT DOCUMENTS 5,142,047 * 8/1992 Summerton et al. ................. 544/118

FOREIGN PATENT DOCUMENTS

9402603 * 3/1994 (WO) .

OTHER PUBLICATIONS

I. Edery et al., "An Efficient Strategy to Isolate Full–Length cDNAs Based on an mRNA Cap Retention Procedure (CAPture)", Molecular and Cellular Biology vol. 15, No. 6, Jun. 1995, p. 3363–3371.

K. Maruyama et al., "Oligo–capping: a simple method to replace the cap structure of eukaryotic mRNAs with oligoribouncleotides", Gene, 138, 1994 p. 171–174.

S. Kato et al., "Construction of a human full–length cDNA bank", Gene, 150, 1994, p. 243–250.

* cited by examiner

Primary Examiner—Robert A. Schwartzman
Assistant Examiner—Sean McGarry
(74) Attorney, Agent, or Firm—Griffin & Szipl, P.C.

(57) ABSTRACT

Disclosed is a method for making full-length CDNA libraries, which is for making libraries of cDNAs having a length corresponding to a full-length of mRNAs and comprises the following steps of; binding a tag molecule to a diol structure present in 5' Cap ($^{7Me}G_{ppp}N$) sites of mRNAs, forming RNA-DNA hybrids by reverse transcription using primers such as oligo dT and the mRNAs connected with the tag molecule as templates, and separating RNA-DNA hybrids carrying a DNA corresponding to a full-length of mRNAs from the RNA-DNA hybrids formed above by using function of the tag molecule. To obtain mRNA connected with a tag molecule, the diol structure present in 5' Cap site of mRNA is subjected to a ring-open reaction by oxidation with sodium periodate to form a dialdehyde and the dialdehyde is reacted with a tag molecule having a hydrazine terminus. According to the present invention, there are provided a novel method capable of efficiently labeling 5' Cap site and a method for making full-length cDNA libraries utilizing the labeling method.

25 Claims, 9 Drawing Sheets

Fig. 5

Efficiency of cDNA library production

10μg mouse brain mRNA

↓ Biotinylation
  I strand cDNA synthesis

~3.5μg 1st strand cDNA

↓ Full length cDNA capture

~350ng cDNA

↓ Release from beads with RNaseH
  Oligo dG - tailing
  II strand cDNA synthesis 200ng ds cDNA ↓ Restriction digestion
  Cloning in λ ZapII 2×10⁶ Recombinant plaques PCR amplification of 5'end of insulin-receptor mRNA (5.2kb) after selection of full length cDNA M: Marker (PCR product)
1: unselected first strand cDNA
2: fraction not bound by beads
3: captured (full length) cDNA

Fig. 8

```
5'                     ACAGCCGCATCTTCTTGTGCAGTGCCAGCCTCGTCCCGTAGACAAAATGGTGAAGGTCG
    GAPDH
    18F.1   GCTCTCTGCTCCTCCCCTGTTCCAGAGACGGGCCGCATCTTCTTGTGCAGTGCCAGCCTCGTCCCGTAGACAAAATGGTGAAGGTCG
    20F.1   GCTCTCTGCTCCTCCCCTGTTCCAGAGACAGCCGCATCTTCTTGTGCAGTGCCAGCCTCGTCCCGTAGACAAAATGGTGAAGGTCG
    22F.1   GCTCTCTGCTCCTCCCCTGTTCCAGAGACGGCCGCATCTTCTTGTGCAGTGCCAGCCTCGTCCCGTAGACAAAATGGTGAAGGTCG

GAPDH   GTGTGAACGGATTTGGCCGTATTGGGCGCCTGGTCACCAGGGCTGCCATTTGCAGTGGCAAAGTGGAGATTGTTGCCATCAACGA
    18F.1   GTGTGAACGGATTTGGCCGTATTGGGCGCCTGGTCACCAGGGCTGCCATTTGCAGTGGCAAAGTGGAGATTGTTGCCATCAACGA
    20F.1   GTGTGAACGGATTTGGCCGTATTGGGCGCCTGGTCACCAGGGCTGCCATTTGCAGTGGCAAAGTGGAGATTGTTGCCATCAACGA
    22F.1   GTGTGAACGGATTTGGCCGTATTGGGCGCCTGGTCACCAGGGCTGCCATTTGCAGTGGCAAAGTGGAGATTGTTGCCATCAACGA

GAPDH   CCCCTTCATTGACCTCAACTACATGGTCTACATGTTCCAGTATGACTCCACTCACGGCAAATTCAACGGCACAGTCAAGGCCGAG
    18F.1   CCCCTTCATTGACCTCAACTACATGGTCTACATGTTCCAGTATGACTCCACTCACGGCAAATTCAACGGCACAGTCAAGGCCGAG
    20F.1   CCCCTTCATTGACCTCAACTACATGGTCTACATGTTCCAGTATGACTCCACTCACGGCAAATTCAACGGCACAGTCAAGGCCGAG
    22F.1   CCCCTTCATTGACCTCAACTACATGGTCTACATGTTCCAGTATGACTCCACTCACGGCAAATTCAACGGCACAGTCAAGGCCGAG

GAPDH   AATGGGAAGCTTGTCATCAA
    18F.1   AATGGGAAGCTTGTCATCAA
    20F.1   AATGGGAAGCTTGTCATCAA
    22F.1   AATGGGAAGCTTGTCATCAA
```

SEQ ID NO: 1
SEQ ID NO: 2
SEQ ID NO: 3
SEQ ID NO: 4

Fig. 9

```
                 GTGGGTGCAGCGAACTTTATTGATGGTATTCAAGAGAGTAGGGAGGGCTCCCTAGGCCCCTCCTGTTATTATGGG
GAPDH
18F.1   TTTTTTTTTTGGGTGCAGCGAACTTTATTGATGGTATTCAAGAGAGTAGGGAGGGCTCCCTAGGCCCCTCCTGTTATTATGGG
20F.1   TTTTTTTTTTGGGTGCAGCGAACTTTATTGATGGTATTCAAGAGAGTAGGGAGGGCTCCCTAGGCCCCTCCTGTTATTATGGG
22F.1   TTTTTTTTTTGGGTGCAGCGAACTTTATTGATGGTATTCAAGAGAGTAGGGAGGGCTCCCTAGGCCCCTCCTGTTATTATGGG

GAPDH   GGTCTGGGATGGAAATTGTGAGGGAGATGCTCAGTGTTGGGGGCCGAGTTGGGATAGGGCCTCTCTTGCTCAGTGTCCTTGCTGG
18F.1   GGTCTGGGATGGAAATTGTGAGGGAGATGCTCAGTGTCAGTGTTGGGGGCCGAGTTGGGATAGGGCCTCTCTTGCTCAGTGTCCTTGCTGG
20F.1   GGTCTGGGATGGAAATTGTGAGGGAGATGCTCAGTGTCAGTGTTGGGGGCCGAGTTGGGATAGGGCCTCTCTTGCTCAGTGTCCTTGCTGG
22F.1   GGTCTGGGATGGAAATTGTGAGGGAGATGCTCAGTGTCAGTGTTGGGGGCCGAGTTGGGATAGGGCCTCTCTTGCTCAGTGTCCTTGCTGG

GAPDH   GGTGGGTGGTCCAGGGTTTCTTA
18F.1   GGTGGGTGGTCCAGGGTTTCTTA
20F.1   GGTGGGTGGTCCAGGGTTTCTTA
22F.1   GGTGGGTGGTCCAGGGTTTCTTA
```

SEQ ID NO: 5
SEQ ID NO: 6
SEQ ID NO: 7
SEQ ID NO: 8

3'

SEQUENCE LISTING

<160> NUMBER OF SEQ ID NOS: 8

<210> SEQ ID NO 1
<211> LENGTH: 249
<212> TYPE: DNA
<213> ORGANISM: mouse

<400> SEQUENCE: 1

```
acagccgcat cttcttgtgc agtgccagcc tcgtcccgta gacaaaatgg tgaaggtcgg      60
tgtgaacgga tttggccgta ttgggcgcct ggtcaccagg gctgccattt gcagtggcaa     120
```

```
agtggagatt gttgccatca acgacccctt cattgacctc aactacatgg tctacatgtt    180
ccagtatgac tccactcacg gcaaattcaa cggcaccgtc aaggccgaga atgggaagct    240
tgtcatcaa                                                           249

<210> SEQ ID NO 2
<211> LENGTH: 275
<212> TYPE: DNA
<213> ORGANISM: mouse

<400> SEQUENCE: 2
gctctctgct cctccctgtt ccagagacgg ccgcatcttc ttgtgcagtg ccagcctcgt     60
cccgtagaca aaatggtgaa ggtcggtgtg aacggatttg gccgtattgg gcgcctggtc    120
accagggctg ccatttgcag tggcaaagtg gagattgttg ccatcaacga ccccttcatt    180
gacctcaact acatggtcta catgttccag tatgactcca ctcacggcaa attcaacggc    240
acagtcaagg ccgagaatgg gaagcttgtc atcaa                              275

<210> SEQ ID NO 3
<211> LENGTH: 275
<212> TYPE: DNA
<213> ORGANISM: mouse

<400> SEQUENCE: 3
gctctctgct cctccctgtt ccagagacag ccgcatcttc ttgtgcagtg ccagcctcgt     60
cccgtagaca aaatggtgaa ggtcggtgtg aacggatttg gccgtattgg gcgcctggtc    120
accagggctg ccatttgcag tggcaaagtg gagattgttg ccatcaacga ccccttcatt    180
gacctcaact acatggtcta catgttccag tatgactcca ctcacggcaa attcaacggc    240
acagtcaagg ccgagaatgg gaagcttgtc atcaa                              275

<210> SEQ ID NO 4
<211> LENGTH: 275
<212> TYPE: DNA
<213> ORGANISM: mouse

<400> SEQUENCE: 4
gctctctgct cctccctgtt ccagagacgg ccgcatcttc ttgtgcagtg ccagcctcgt     60
cccgtagaca aaatggtgaa ggtcggtgtg aacggatttg gccgtattgg gcgcctggtc    120
accagggctg ccatttgcag tggcaaagtg gagattgttg ccatcaacga ccccttcatt    180
gacctcaact acatggtcta catgttccag tatgactcca ctcacggcaa attcaacggc    240
acagtcaagg ccgagaatgg gaagcttgtc atcaa                              275

<210> SEQ ID NO 5
<211> LENGTH: 183
<212> TYPE: DNA
<213> ORGANISM: mouse

<400> SEQUENCE: 5
gtgggtgcag cgaactttat tgatggtatt caagagagta gggagggctc cctaggcccc     60
tcctgttatt atgggggtct gggatggaaa ttgtgaggga gatgctcagt gttggggcc     120 gagttgggat agggcctctc ttgctcagtg tccttgctgg ggtgggtggt ccagggtttc    180
tta                                                                 183
```

```
<210> SEQ ID NO 6
<211> LENGTH: 193
<212> TYPE: DNA
<213> ORGANISM: mouse

<400> SEQUENCE: 6
tttttttttt ttgggtgcag cgaactttat tgatggtatt caagagagta gggagggctc      60
cctaggcccc tcctgttatt atgggggtct gggatggaaa ttgtgaggga gatgctcagt     120
gttgggggcc gagttgggat agggcctctc ttgctcagtg tccttgctgg ggtgggtggt     180
ccagggtttc tta                                                        193

<210> SEQ ID NO 7
<211> LENGTH: 192
<212> TYPE: DNA
<213> ORGANISM: mouse

<400> SEQUENCE: 7
tttttttttt tgggtgcagc gaactttatt gatggtattc aagagagtag ggagggctcc      60
ctaggcccct cctgttatta tggggtctg ggatggaaat tgtgagggag atgctcagtg     120
ttgggggccg agttgggata gggcctctct tgctcagtgt ccttgctggg gtgggtggtc     180
cagggtttct ta                                                         192

<210> SEQ ID NO 8
<211> LENGTH: 192
<212> TYPE: DNA
<213> ORGANISM: mouse

<400> SEQUENCE: 8
tttttttttt tgggtgcagc gaacttatt gatggtattc aagagagtag ggagggctcc      60
ctaggcccct cctgttatta tggggtctg ggatggaaat tgtgagggag atgctcagtg     120
ttgggggccg agttgggata gggcctctct tgctcagtgt ccttgctggg gtgggtggtc     180
cagggtttct ta                                                         192
```

METHOD FOR MAKING FULL-LENGTH CDNA LIBRARIES

BACKGROUND OF THE INVENTION (1) Field of the Invention

The present invention relates to a method for making full-length cDNA libraries. More in detail, it relates to a method for making full-length CDNA libraries by a method for purification of full-length cDNAs utilizing chemical modification of mRNAs.

(2) Related Art

Methods for synthesizing cDNAs are essential techniques for researches in the fields of medical science and biology as an indispensable method for analyzing gene transcripts. Any DNA genetic information manifests physiological activity through transcripts and a potential means for analyzing such transcripts is cDNA cloning. In cDNA syntheses according to conventional methods, clones are ultimately isolated from a cDNA library prepared from poly A sites by using oligo dT as a primer. However, in most cases using such a method, whole structures of transcription units cannot be analyzed since the transcription units are not synthesized in their full-lengths. Therefore, when using a conventional cDNA library, it is essential for analysis of gene structures in their full-lengths to synthesize 5' upstream regions by the primer elongation method, or perform gene working of the 5' upstream regions by cDNA synthesis using a random primer.

However, such conventional methods for synthesizing cDNAs as described above have, for example, the following problems.

1. cDNAs covering most part of transcripts can be obtained by using a random primer. However, those cDNAs are short fragments and clones covering from the poly A site to 5' Cap site cannot be isolated.
2. Any cDNA obtained by using oligo dT as a primer contains 3' end. However, because the reverse transcriptase cannot reach the 5' Cap site, the 5' upstream should be further isolated and analyzed by the primer elongation method and 5'RACE or the like.
3. Efficiency of any conventional methods for isolating cDNAs in their full-lengths including those methods mentioned above is not sufficient (only 2, 000, 000 recombinant phages can be obtained from 100 μg of mRNA). Therefore, more efficient techniques are desired for practical purposes.

As conventional methods for synthesizing full-length cDNAs, the following methods can be mentioned; the method utilizing a Cap binding protein of yeast or Hela cells for labeling the 5' Cap site (I. Edery et al., "An Efficient Strategy To Isolate Full-length cDNAs Based on an mRNA Cap Retention Procedure (CAPture)", MCB, 15, 3363–3371, 1995); the method where phosphates of incomplete cDNAs without 5' Cap are removed by using alkaline phosphatase and then the whole cDNAs are treated with de-capping enzyme of tobacco mosaic virus so that only the full-length cDNAs have phosphates (K. Maruyama et al., "Oligo-capping: a simple method to replace the cap structure of eukaryotic mRNAs with oligoribonucleotides", Gene, 138, 171–174, 1995., S. Kato et al., "Construction of a human full-length cDNA bank", Gene, 150, 243–250, 1995) and the like.

The reasons why efficiency of these conventional methods for synthesizing full-length cDNAs is not sufficient include, for example, the followings.

① Because the recognition of 5' Cap site depends on reactions of proteins like adenovirus Cap binding protein and the de-capping enzyme of tobacco mosaic virus, high efficiency of the selection of full-length cDNAs (RNAs) cannot be expected.

② When the first strand of cDNA is synthesized by a reverse transcriptase, the synthesized strand does not extend to the 5' Cap site.

③ There are also problems of the addition of primer sequences, synthesis efficiency of second strand, and cloning efficiency of double stranded cDNA after the synthesis of the first strand.

As described above, in the production of cDNA libraries in a multi-step process, there are problems such as those mentioned as ① to ③ above.

Therefore, an object of the present invention is to provide a novel method in which 5' Cap site can be more efficiently labeled compared with the labeling by the proteins reactions such as those by the conventional adenovirus Cap binding protein and the de-capping enzyme of tobacco mosaic virus.

Another object of the present invention is to provide a method for making full-length cDNA libraries utilizing the novel method of the present invention for labeling of the 5' Cap site.

SUMMARY OF THE INVENTION

The present invention relates to a method for making full-length CDNA libraries, which is for making libraries of cDNAs having a length corresponding to full-length mRNAs and comprises the following steps of;

binding a tag molecule to a diol structure present in 5' Cap ($^{7Me}G_{ppp}N$) sites of mRNAs, forming RNA-DNA hybrids by reverse transcription using primers and the mRNAs connected with the tag molecule as templates, and separating RNA-DNA hybrids carrying a DNA corresponding to full-length mRNAs from the RNA-DNA hybrids formed above by using function of the tag molecule.

BRIEF DESCRIPTION OF DRAWINGS

FIG. 5 is a scheme showing efficiency of synthesis of full-length cDNA library.

Upper part: colony hybridization pattern (left; probe of 5' region, right: probe of 3' region).

Lower part: a map of GAPDH mRNA 1228BP.

FIG. 8 shows sequences of 5' end of GAPDH(SEQ ID. NO: 1). This figure shows three nucleotide sequences of cDNA clones (18.1SEQ IS, 20.1, 22.1SEQ ID NOS:2–4)

selected by using cDNA clones of GAPDH as probes. The three clones had nucleotide sequences longer than the 5' nucleotide sequences previously reported.

FIG. 9 shows sequences of 3' end of GAPDH(SEQ ID NO:5). This figure shows three nucleotide sequences of cDNA clones (18.1, 20.1, 22.1SEQ ID NO:6–8) selected by using cDNA clones of GAPDH as probes. They include oligo primers used for the synthesis of full-length cDNAs.

DESCRIPTION OF THE INVENTION

Figure 1:
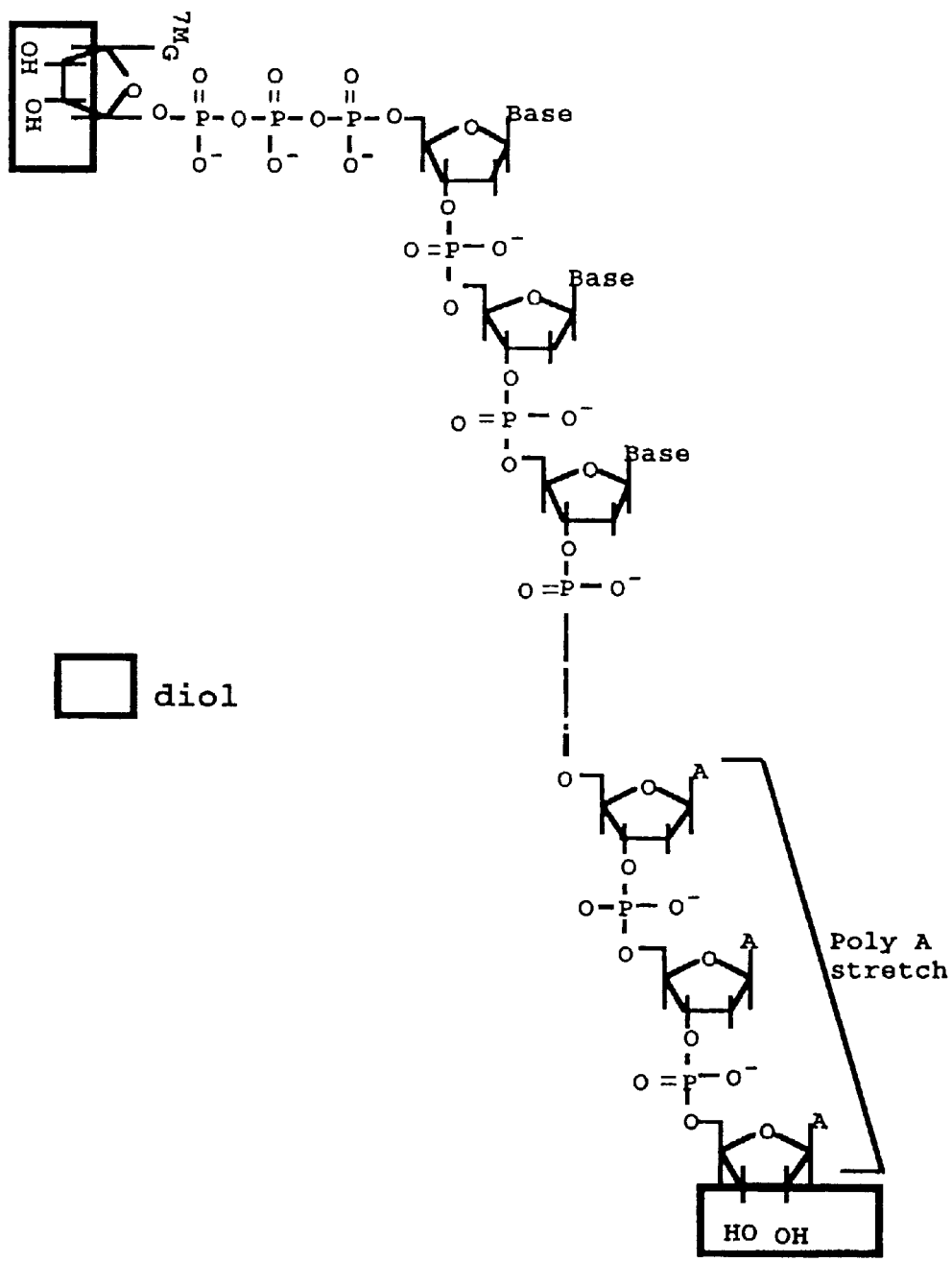
FIG. 1 shows a structure of mRNA having diol structures at its both ends (5' Cap site and 3' site).

According to the method of the present invention, 5' Cap site is labeled by chemical synthesis utilizing the structure specific for the 5' Cap site, the diol structure, in order to enhance the recognition of the 5' Cap site and to increase efficiency of the selection of full-length cDNAs (RNAs) (see FIG. 1).

That is, according to the method of the present invention, a tag molecule is first bound to a diol structure present in 5' Cap ($^{7Me}G_{ppp}N$) site of mRNAs. This tag molecule is chemically bound to the 5' Cap site, and full-length cDNAs are synthesized by using mRNAs labeled with the tag molecule as a template to produce full-length cDNA library.

Figure 2:
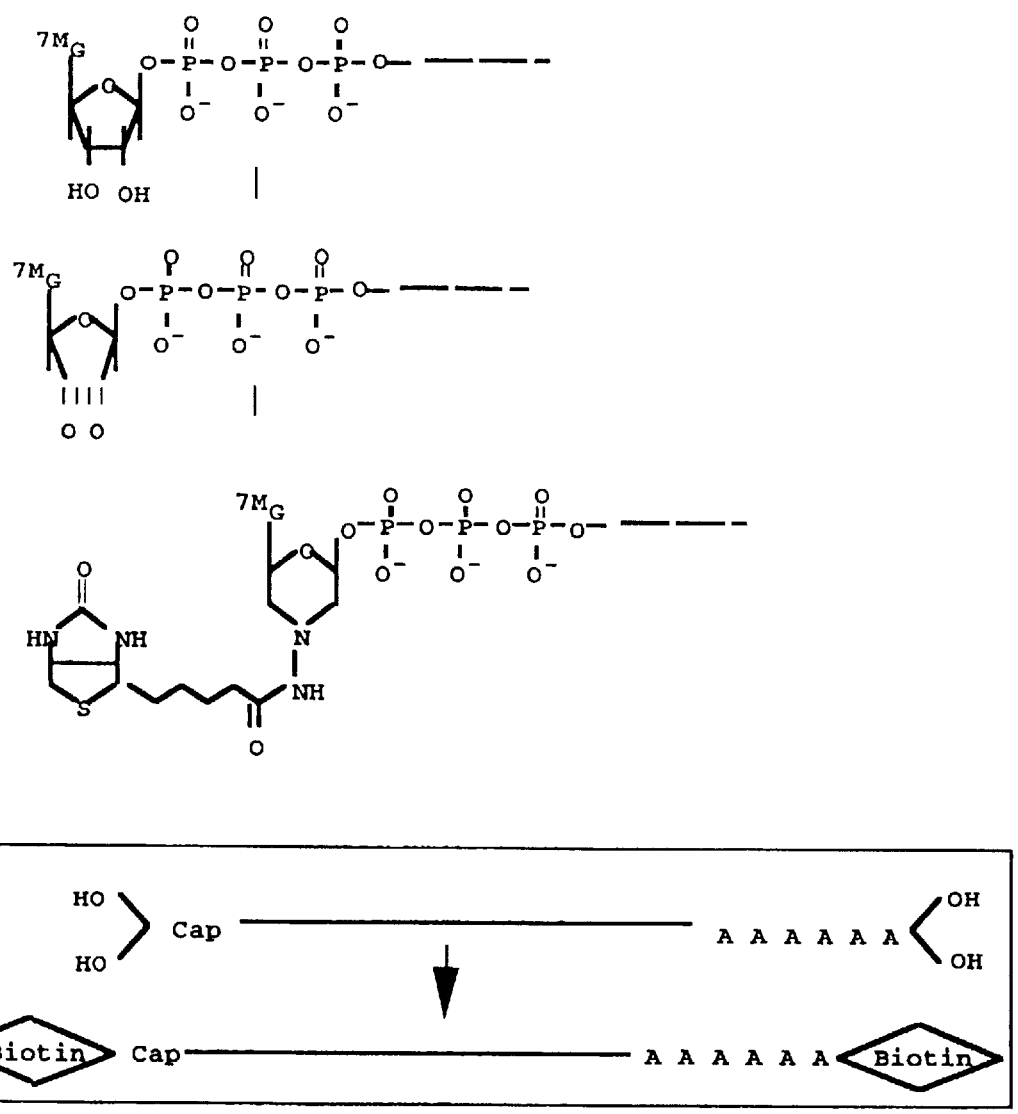
FIG. 2 shows a reaction scheme representing oxidation of the diol structure of 5' Cap site of MRNA and addition of biotin hydrazide thereto.

The binding of the tag molecule to the 5' Cap site can be obtained by, for example, oxidation ring-opening reaction of the 5' Cap site diol structure with an oxidizing agent such as sodium periodate ($NaIO_4$) to form a dialdehyde and subsequent reaction of the dialdehyde with a tag molecule having a hydrazine terminus, as shown in FIG. 2.

As the tag molecule having a hydrazine terminus, for example, biotin molecule or avidin molecule having a hydrazine terminus can be mentioned. A molecule showing reaction specificity such as antigens or antibodies can also be used as the tag molecule. That is, the specific label used as the tag molecule is not particularly limited.

Figure 3:
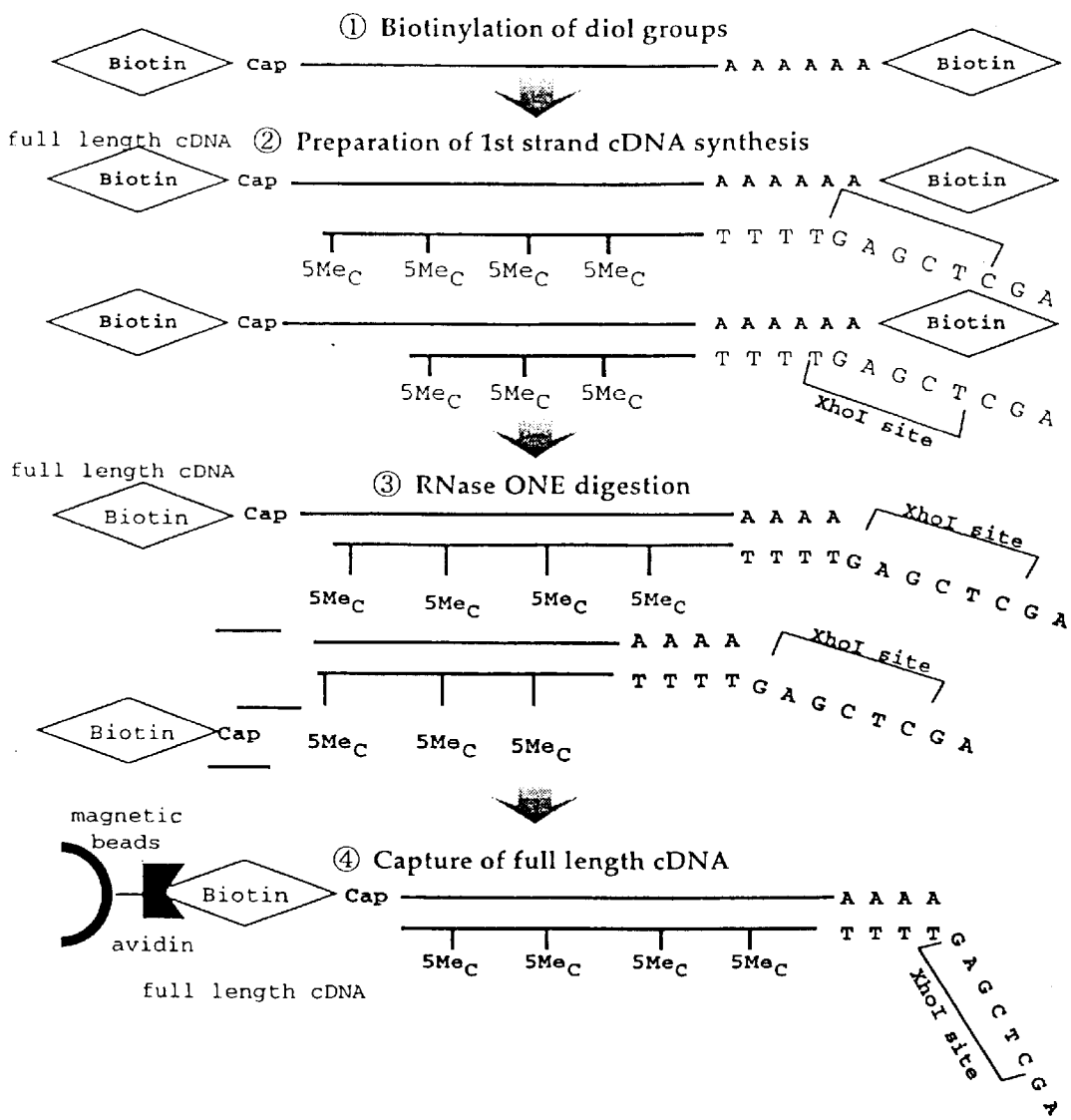
FIG. 3 is a scheme showing each step of the method for making full-length cDNAs (the first half).
Figure 4:
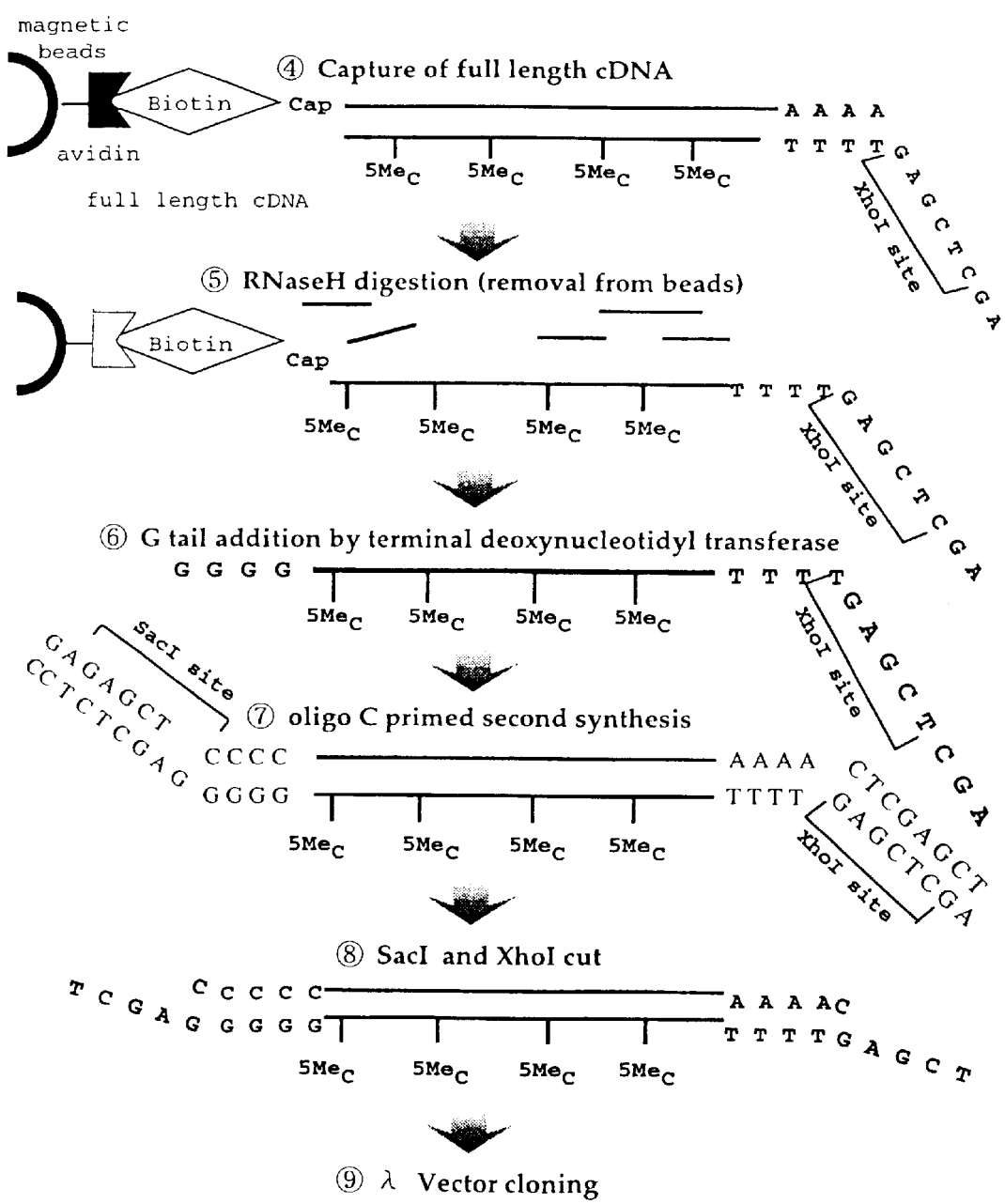
FIG. 4 is a scheme showing each step of the method for making full-length cDNAs (the latter half).

Exemplary process steps including ① binding of tag molecule to ⑨ cloning of full-length cDNAs (tag molecule: biotin) are shown in FIGS. 3 and 4.
① Biotinylation of diol groups
② Preparation of first cDNA strand
③ Ribonuclease I (RNase I) Digestion
④ Capture of full-length cDNA hybrids (with avidin beads)
⑤ RNase H digestion (removal from the avidin beads)
⑥ G tail addition by terminal deoxynucleotidyl transferase
⑦ Preparation of second strand primed with oligo C
⑧ Cleavage with Sac I and Xho I
⑨ Cloning with λ vector The RNA-DNA hybrids can be produced by reverse transcription starting from a primer such as oligo dT using the mRNAs labeled with the bound tag molecule as a template. This production of RNA-DNA hybrids by reverse transcription utilizing a primer such as oligo dT can be performed by a conventional method.

Further, RNA-DNA hybrids carrying a DNA corresponding to a full-length of mRNAs are separated from the whole RNA-DNA hybrids by using function of the tag molecule.

Specifically, the tag molecule is removed from those RNA-DNA hybrids carrying a DNA not corresponding to a full-length of mRNAs by digesting the hybrids with an RNase capable of cleaving single strand RNA to cleave the single strand parts of the hybrids. Then, those hybrids carrying a DNA corresponding to a full-length of mRNAs (full-length cDNAs extended to 5' Cap) are separated by utilizing the function of the tag molecule.

For example, when the tag molecule is biotin molecule, hybrids carrying a DNA corresponding to a full-length of mRNAs can be separated by allowing the biotin molecules possessed by the RNA-DNA hybrids as the tag molecule to react with avidin fixed on a solid support. When the tag molecule is avidin molecule, hybrids carrying a DNA corresponding to a full-length of mRNA can be separated by allowing the avidin molecules possessed by the RNA-DNA hybrids as the tag molecule to react with biotin fixed on a solid support.

Therefore, one embodiment of the present invention relates to a method for making full-length cDNA libraries, which is for making libraries of cDNAs having a length corresponding to a full-length of mRNAs and comprises the following steps of;

binding a biotin molecule to a diol structure present in 5' Cap ($^{7Me}G_{ppp}N$) site of mRNAs, forming RNA-DNA hybrids by reverse transcription using primers and the mRNAs connected with biotin molecule as templates, digesting the formed hybrids with an RNase capable of cleaving single strand RNA to cleave the single strand RNA parts of the hybrids to remove biotin molecules from the hybrids, and separating RNA-DNA hybrids carrying a DNA corresponding to a full-length of mRNAs and binding the biotin molecules by allowing them to react with avidin fixed on a solid support.

Another embodiment of the present invention relates to a method for making full-length cDNA libraries, which is for making libraries of cDNAs having a length corresponding to a full-length of mRNAs and comprises the following steps of;

binding an avidin molecule to a diol structure present in 5' Cap ($^{7Me}G_{ppp}N$) site of mRNAs, forming RNA-DNA hybrids by reverse transcription using primers and the mRNAs connected with the avidin molecule as templates, digesting the formed hybrids with an RNase capable of cleaving single strand RNA to cleave the single strand RNA parts of the hybrids to remove avidin molecules from the hybrids, and separating RNA-DNA hybrids carrying a DNA corresponding to a full-length of mRNAs and binding avidin molecules by allowing them to react with biotin fixed on a solid support.

As the RNase capable of cleaving single strand RNA, for example, ribonuclease I can be mentioned. Selection of the hybrids carrying a DNA corresponding to a full-length of mRNA from the whole RNA-DNA hybrids can be performed by any means other than those using an enzyme capable of cleaving single strand RNA. That is, the method for selecting the hybrids is not particularly limited.

According to the method of the present invention, cDNAs are further collected from the separated hybrids carrying DNAs corresponding to full-lengths of mRNAs. The collection of the cDNAs can be performed by, for example, treating the separated hybrids carrying DNAs corresponding to full-lengths of mRNAs with alkaline phosphatase of tobacco mosaic virus. The collection of the cDNAs can also be performed by treating the hybrids carrying DNAs corresponding to full-lengths of mRNAs with an RNase capable of cleaving DNA-RNA hybrids. As such the RNase capable of cleaving DNA-RNA hybrids, for example, RNase H can be mentioned.

A full-length cDNA library can be obtained by synthesizing the second cDNA strands using the collected first cDNA strands as templates and cloning the obtained the second cDNA strands. The second cDNA strands can be synthesized by using cDNAs obtained by, for example, ligating an RNA or DNA oligomer to the 3' end of the first cDNA strands as a template and another oligomer complementary to the former ligated oligomer as a primer. Alternatively, the second cDNA strands can also be synthesized by using cDNAs obtained through ligation of poly G, poly C, poly A or poly T to the 3' end of the first cDNA strands with a terminal nucleotide transferase as a template and respectively complementary oligo C, oligo G, oligo T or oligo A as a primer.

That is, the synthesis of the second cDNA strands can be performed by any suitable method such as the homopolymer method using terminal deoxynucleotidyl transferase and a method comprising ligating, by an RNA ligase, a single strand primer to the 3' end of the first CDNA or 5' strand of mRNA of which 5' Cap has been removed and extending the strand with a polymerase, and therefore the method for synthesizing the second strand is not particularly limited.

According to the present invention, full-length cDNAs can be efficiently selected by chemically modifying the 5' Cap site of mRNA. This is advantageous because low background and extremely high efficiency can be obtained due to the fact that the modification for the recognition of the 5' Cap site does not depend on enzymatic reactions at all but depends on the chemical reactions utilizing the diol residue specific for the structure of the 5' Cap site of mRNA.

In the method of the present invention, the collection of full-length cDNAs can be performed in a solid phase system utilizing RNase I treatment and biotin-avidin reaction, which can show high selection specificity. Therefore, the method enables the production of libraries by mass productive robotics.

EXAMPLE

The method described in this example comprised the steps outlined in FIGS. 3 and 4, i.e., the following steps.
① Biotinylation of diol groups
② Preparation of first cDNA strand
③ Ribonuclease I (RNase I) Digestion
④ Capture of full-length cDNA hybrids (with avidin beads)
⑤ RNase H digestion (removal from the avidin beads)
⑥ G tail addition by terminal deoxynucleotidyl transferase
⑦ Preparation of second strand primed with oligo C
⑧ Cleavage with Sac I and Xho I
⑨ Cloning with λ vector Preparation of RNA Slices of brain tissue (0.5–1 g) were homogenized in 10 ml of a suspension and extracted with 1 ml of 2M sodium acetate (pH 4.0) and the same amount of a mixture of phenol/chloroform (volume ratio 5:1). After the extraction, the same volume of isopropanol was added to the aqueous layer to precipitate RNA. This sample was incubated on ice for an hour and centrifuged at 4000 rpm for 15 minutes with cooling to collect the precipitates. The precipitates were washed with 70% ethanol and dissolved in 8 ml of water. By adding 2 ml of 5M NaCl and 16 ml of an aqueous solution (pH 7.0) containing 1% CTAB (cetyltrimethylammonium bromide), 4M urea, and 50 mM Tris, RNA was precipitated and polysaccharides were removed (CTAB precipitate). After centrifugation at 4000 rpm for 15 minutes at room temperature, the RNA was dissolved in 4 ml of 7M guanidine-Cl. Then, two-fold amount of ethanol was added to the solution, incubated for an hour on ice and centrifuged at 4000 rpm for 15 minuets. The resulting precipitates were washed with 70% ethanol and collected. The precipitates were again dissolved in water and purity of RNA was determined by measuring OD ratio 260/280 (>1.8) and 230/260 (<0.45).

Binding of biotin to diol residues of RNA (FIG. 2, step ①)

A two-step reaction, i.e., oxidation of the diol residues and subsequent coupling reaction of biotin hydrazide (Sigma) with the oxidized RNA, was performed to bind biotin to diol residues of RNA (CAP and 3' end of RNA).

First, 10–20 μg of mRNA is treated in 50 μl of 66 mM sodium acetate buffer (pH 4.5) containing sodium periodate as an oxidizing agent. This oxidation reaction is performed on ice under light-shielding condition for 45 minutes. Then, the mixture is added with 5 μl of 5M lithium chloride, 1 μl of 10% SDS and the same amount of isopropanol, incubated at –20° C. for 30 minutes and centrifuged at 15000 rpm at 4° C. for 15 minutes to afford RNA precipitates. The RNA precipitates are washed with 70% ethanol and dissolved again in 50 μl of RNase-free water. To this sample, 5 μl of 1M sodium oxide (pH 6.1), 5 μl of 10% SDS and 150 μl of 10 mM biocytin hydrazide (an aqueous solution) are added and the mixture is incubated over night at room temperature (22–26° C.). Thereafter, the sample is added with 5 μl of 5M NaCl, 7.5 μl of 1M sodium acetate (pH 6.1) and 2.5-fold volume of ethanol, and incubated for an hour on ice. The biotinylated RNA is precipitated again by centrifugation at 4° C. for 15 minutes. The RNA precipitates were washed once with 70% ethanol and then with 80% ethanol. Finally, the RNA precipitates are dissolved again in RNase-free water and used for preparation of the first cDNA strand.

Preparation of the first cDNA strand (FIG. 2, step ②)

Reverse transcription reaction was performed by using 10 μl of the biotinylated mRNA and 2000 units of Superscript II (Gibco BRL) in 100 μl of a buffer (50 mM Tris-HCl, 75 mM KCl, 3 mM MgCl$_2$, 10 mM DTT) in the presence of 0.5 mM 5-methyl-dCTP, 1 mM DATP, 1 mM dTTP and 1 mM dGTP. 5 μg of oligonucleotide was used as a primer. The reaction was performed at 42° C. for 45 minutes, then the reaction solution was incubated at 50' C. for 20 minutes. At the beginning of this reaction, 20 μl of the reaction solution was collected and, to the collected solution, 1 μl of [α-$^{32}$P]-dGTP (3000 Ci/mmol, 10 μCi/μl, Amersham) was added to determine synthesis yield of the first cDNA strand. 0.5 μl of the RI labeled reaction solution (20 μl) was spotted on DE-81 paper, and RI activity was measured before and after the paper was washed three times with 0.5M sodium phosphate (pH 7.0).

RNase protection of full-length cDNA (FIG. 2, step ③)

mRNAs paired with cDNAs which had not been completely extended by the reverse transcription and the biotin residues labeled at the 3' end of mRNAs were removed by treatment with RNase ONET™ (Promega) which can digest single stranded RNAs at any nucleotide site. More specifically, when the first cDNA strand was synthesized, 20 μl of an RI labeled reaction solution and 80 μl of an unlabeled reaction solution were pooled together, and the sample was incubated at 30° C. for 30 minutes with 40 μl of an RNase I buffer, 355 μl of water and 50 units of the RNase I.

Collection of full-length cDNA (FIG. 2, steps ④ and ⑤)

In order to avoid non-specific adsorption to avidin coated magnetic beads, 2.5 mg of yeast tRNA (pre-treated with DNase I) was added to the beads, and the mixture was made 500 μl in volume and incubated on ice for an hour. The cDNAs treated with RNase I were added to the above pre-treated beads and the magnetic beads were incubated in a buffer containing 0.25 M EDTA and 0.5 M NaCl (pH 8.0) at room temperature for 15 minutes with occasional shaking so that the beads should not precipitate. Then, the beads were washed with 0.5 M EDTA (pH 8.0) four times, with 0.4% SDS once and with nuclease-free water three times.

After the sample was treated with 2 units of RNase H in 100 μl of an RNase H buffer at 37° C. for 30 minutes, full-length cDNAs were removed from the beads by incubation of the beads with 0.1% SDS. cDNAs which had not been separated due to incomplete treatment with RNase H could be collected by alkaline hydrolysis in a Tris-formate buffer (pH 9.0) at 65° C. for 10 minutes. The collected full-length single strand cDNAs were extracted once with phenol/chloroform and subjected to G25/G50 Sephadex chromatography. Fractions showing RI activity were collected in an Eppendorf tube having a silicon coated surface and the sample volume was decreased to 10 μl by vacuum suction.

Oligo dG tailing of single strand cDNA (FIG. 2, steps ⑥ and ⑦)

In order to add oligo dG to the collected single strand cDNAs, reaction using 32 units of deoxynucleotidyl transferase (Takara) was conducted in 50 μl of a buffer containing 200 mM Na cacodylate, 1 mM $MgCl_2$, 1 mM $CoCl_2$, 1 mM 2-mercaptoethanol and 100 μM dGTP (pH 6.9) at 37° C. for 30 minutes. EDTA was added to a final concentration of 50 mM and the cDNAs were extracted with phenol/chloroform and subjected to G25/G100 chromatography. The volume of the recovered dG-tailed cDNA was decreased to 30 μl by vacuum suction.

Synthesis of double-stranded cDNA (FIG. 2, step ⑧)

To the solution containing oligo dG-tailed single strand cDNA, 6 μl of the second strand lower buffer (200 mM Tris-Cl, 100 mM KCl, 100 mM $(NH_4)_2SO_4$, 20 mM $MgSO_4$, 1% Triton X100, 1 mg/ml BSA, pH 8.75), 3 μl of the second strand higher buffer (200 mM Tris-Cl, 600 mM KCl, 20 mM $MgCl_2$, pH 9.2), 600 ng of the second strand primer adapter with a sequence recognizable by restriction enzymes Sac I and Spe I, 0.25 mM dNTP's, 15 units of ExTaq polymerase (Takara), 150 units of Ampligase, thermostable DNA ligase (Epicentre), 3 units of hybridase and thermostable RNase H (Epicentre) were added to afford a solution of a final volume of 60 μl. Temperature of the reaction mixture was controlled by a thermocycler at 55° C. for 5 minutes, then gradually lowered from 55° C. to 35° C. at a rate of 0.3° C./minute, kept at 35° C. for 15 minutes and at 72° C. for 15 minutes for the reaction. Annealing/extension were repeated by incubating the sample at 35° C. for one hour and at 65° C. for 30 minutes. Finally, the sample was extracted with phenol/chloroform and recovered by ethanol precipitation.

Cleavage by restriction enzymes and cloning (FIG. 2, step ⑨)

The cDNAs were treated with endonucleases, restriction enzymes Sac I and Xho I, under standard conditions, and then subjected to Sephadex G25-G100 chromatography. The fractions were collected into a sample tube as described above. Finally, 200 ng of cDNA was inserted into lambda Zap II vector. The vector was prepared in advance in 5 μl of a buffer recommended by the manufacturer, in which Sac I, Xho I, and 200 units of T4 DNA ligase (New England Biolabs) were used.

Evaluation of the resulting library (1) Yield and cloning efficiency

Yields of the steps were shown in Table 1. As shown in FIG. 5, when 10 μg of mRNA was used as a starting material, $2 \times 10^6$ of recombinant plaques were finally collected.

TABLE 1

| Treatment of first strand cDNA | Starting material (cpm) | Recovered product (cpm) | Recovery (%) |
|---|---|---|---|
| Untreated | 18,920 | 17,810 | 94 |
| RNase I | 151,000 | 22,560 | 14.9 |
| TAP (CAP removed) | 5,442 | 3,848 | 69 |
| RNase I + TAP | 14,350 | 235 | 1.6 |
| RNase H | 151,000 | 3,462 | 2.2 |

(2) Evaluation of library

Figure 6:
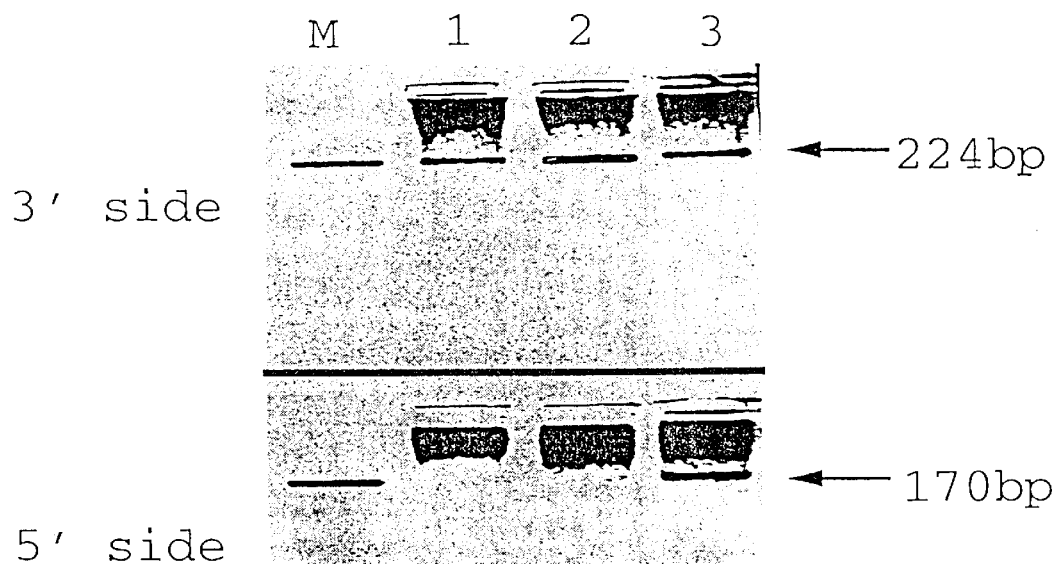
FIG. 6 shows the result of confirming the synthesis of full-length cDNAs by using 5' site and 3' site primers. Presence of full-length cDNA synthesis products was confirmed by using the primers of the both ends for an exemplary mRNA, insulin receptor mRNA.

① As to mRNA of insulin receptor (5.2 kb), it was determined whether or not either 5' end or 3' end of the gene was contained in the library by using 2 primer sets which amplify the 5' end and/or 3' end. As shown in FIG. 6, a 224 bp amplified product of the 3' end was observed and the 170 bp product of the 5' end was not in the case where the single strand cDNAs were not selected and in the fractions which were not bound to the beads. In contrast, the 170 bp product of the 5' end was clearly observed in the full-length library of the present invention.

Figure 7:
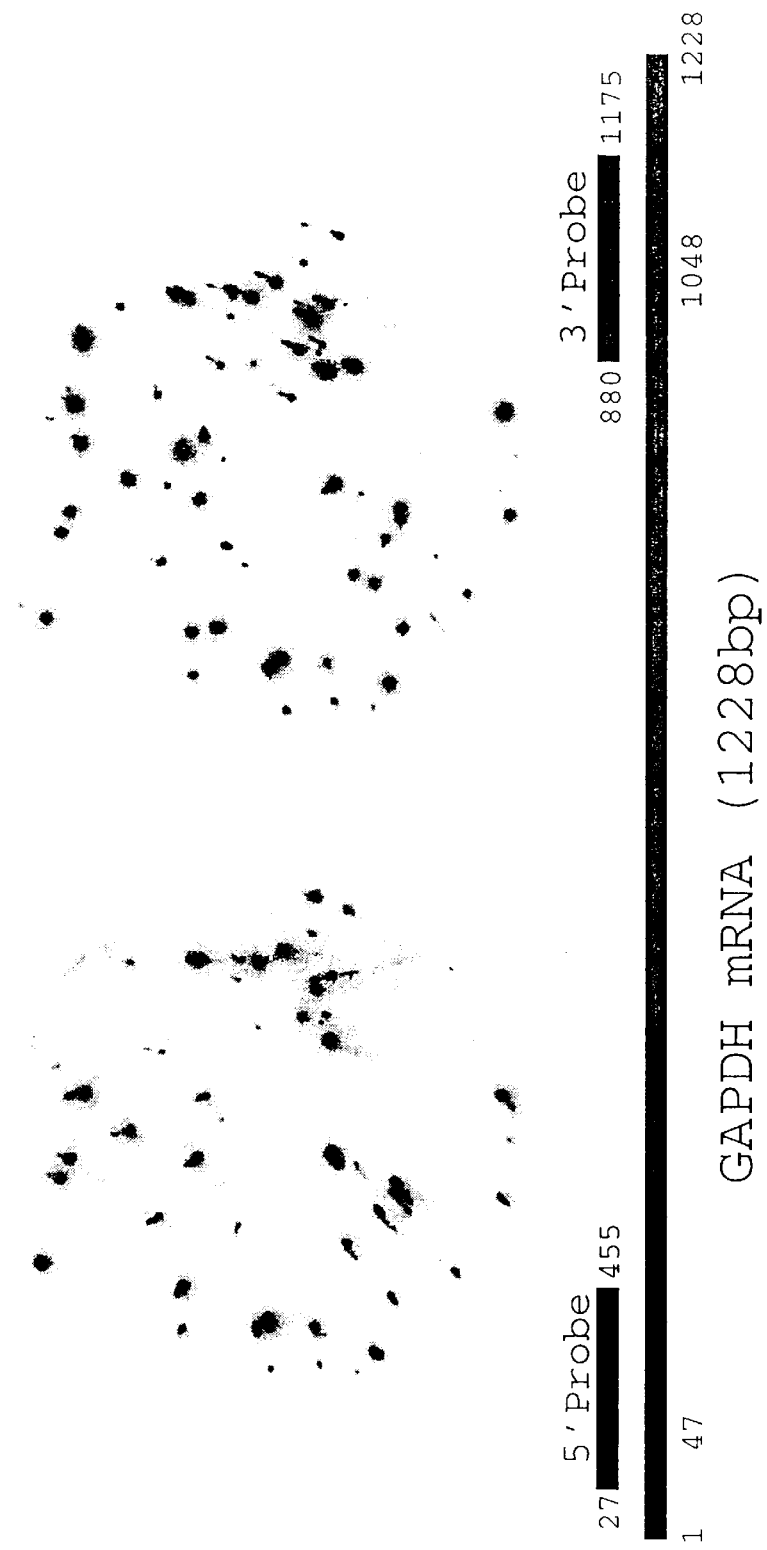
FIG. 7 shows results of colony hybridization utilizing 5' and 3' end clones of GAPDH (glyceraldehyde 3-phosphate dehydrogenase) as probes.

② Terminal nucleotide sequence of GAPDH (Glyceraldehyde 3-phosphate dehydrogenase) gene As shown in FIG. 7, GAPDH gene was hybridized onto a replica filter of the full-length library with 5' end and 3' end probes. Since 80% of the plaques which gave positive signals with the 3' end probe also gave positive signals with the 5' end probe, it was confirmed that 80% of the library consisted of full-length cDNAs.

Three clones were further isolated from them and, after preparing λ phage DNAs, the both ends of the insert were sequenced by ABI377. The results are shown in FIGS. 8 and 9. It is considered that full-length cDNAs have been synthesized at both 5' and 3' ends. The 3' ends were primed from the common site, and 5' end showed C extension/T extension structure, which is specific to Cap site. Therefore, it was confirmed that it was a library containing whole 5' site.

What is claimed is:

1. A method for making full-length cDNA libraries, which is for making libraries of cDNAs having lengths corresponding to full lengths of respective mRNAs, and comprises the following steps of:

binding a tag molecule to a diol structure present in 5' Cap ($^{7Me}G_{ppp}N$) sites of mRNAs by oxidizing the 5' Cap site diol to form a dialdehyde and reacting the resulting dialdehyde with a tag molecule having a group reactive with the dialdehyde, forming RNA-DNA hybrids by reverse transcription using primers and the mRNAs binding the tag molecule as templates, and separating RNA-DNA hybrids carrying a DNA corresponding to a full-length of mRNA from the RNA-DNA hybrids formed above by using a function of the tag molecule.

2. A method of claim 1, wherein the primer is oligo dT.

3. A method of claim 1, wherein the tag molecule is a biotin molecule having a functional group capable of binding to a diol structure present in 5' Cap site of mRNA and the RNA-DNA hybrids carrying a DNA corresponding to a full-length of mRNAs are separated by utilizing binding between an avidin molecule fixed on a solid support and a biotin molecule possessed by the RNA-DNA hybrids as the tag molecule.

4. A method of claim 1, wherein the tag molecule is an avidin molecule having a functional group capable of binding to a diol structure present in 5' Cap site of mRNA and the RNA-DNA hybrids carrying a DNA corresponding to a full-length of mRNAs are separated by utilizing binding between a biotin molecule fixed on a solid support and an avidin molecule possessed by the RNA-DNA hybrids as the tag molecule.

5. A method of claim 1, wherein the diol structure present in 5' Cap site of mRNA is subjected to a ring-open reaction by oxidation with sodium periodate to form a dialdehyde and the dialdehyde is reacted with a tag molecule having a hydrazine terminus to form mRNA binding the tag molecule.

6. A method of claim 5, wherein the tag molecule having a hydrazine terminus is a biotin molecule or avidin molecule having a hydrazine terminus.

7. A method of claim 1, wherein the RNA-DNA hybrids are digested with an RNase capable of cleaving single strand RNA to cleave the single strand parts of the hybrids so that the tag molecule is removed from those hybrids carrying a DNA not corresponding to a full-length mRNAs and then those hybrids carrying a tag molecule and a DNA corresponding to a full-length of mRNAs are separated.

8. A method of claim 7, wherein the RNase capable of cleaving single strand RNA is ribonuclease I.

9. A method for making full-length cDNA libraries, which is for making libraries of cDNAs having lengths corresponding to full lengths of respective mRNAs, and comprises the following steps of:

binding a biotin molecule to a diol structure present in 5' Cap ($^{7Me}G_{ppp}N$) sites of mRNAs by oxidizing the 5' Cap site diol to form a dialdehyde and reacting the resulting dialdehyde with a biotin molecule having a group reactive with the dialdehyde, forming RNA-DNA hybrids by reverse transcription using primers and the mRNAs bound to biotin molecules as templates, digesting the RNA-DNA hybrids with an RNase capable of cleaving single strand RNA to cleave the single strand RNA parts of the hybrids carrying a DNA not corresponding to a full-length mRNA to remove biotin molecules from the hybrids, and separating RNA-DNA hybrids carrying a DNA corresponding to a full-length mRNA and binding the biotin molecules by allowing them to react with avidin fixed on a solid support.

10. A method of claim 9, wherein the primer is oligo dT and the RNase capable of cleaving single strand RNA is ribonuclease I.

11. A method for making full-length cDNA libraries, which is for making libraries of cDNAs having lengths corresponding to full lengths of respective mRNAs, and comprises the following steps of:

binding an avidin molecule to a diol structure present in 5' Cap ($^{7Me}G_{ppp}N$) sites of mRNAs by oxidizing the 5' Cap site diol to form a dialdehyde and reacting the resulting dialdehyde with an avidin molecule having a group reactive with the dialdehyde, forming RNA-DNA hybrids by reverse transcription using primers and the mRNAs bound to avidin molecules as templates, digesting the RNA-DNA hybrids with an RNase capable of cleaving single strand RNA to cleave the single strand RNA parts of the hybrids carrying a DNA not corresponding to full-length mRNAs to remove avidin molecules from the hybrids, and separating RNA-DNA hybrids carrying a DNA corresponding to a full-length mRNA and binding avidin molecules by allowing them to react with biotin fixed on a solid support.

12. A method of claim 11, wherein the primer is oligo dT and the RNase capable of cleaving single strand RNA is ribonuclease I.

13. A method of claim 1, wherein cDNAs are collected from the separate hybrids carrying a DNA corresponding to a full-length of mRNAs.

14. A method of claim 13, wherein cDNAs are collected by treating the separated hybrids carrying a DNA corresponding to a full-length of mRNAs with alkaline phosphatase of tobacco mosaic virus.

15. A method of claim 13, wherein cDNAs are collected by treating the separated hybrids carrying a DNA corresponding to a full-length of mRNAs with an RNase capable of cleaving DNA-RNA hybrids.

16. A method of claim 15, wherein the RNase capable of cleaving DNA-RNA hybrids is RNase H.

17. A method of claim 1, wherein second cDNA strands are synthesized by using the collected first cDNA strands as templates and the obtained second cDNA strands are cloned.

18. A method of claim 17, wherein the second cDNA strands are synthesized by using cDNAs obtained by ligating an RNA or DNA oligomer to the 3' end of the first cDNA strands as templates and oligomers complementary to the ligated oligomers as primers.

19. A method of claim 18, wherein the second cDNA strands are synthesized by using cDNAs obtained through ligation of poly G, poly C, poly A or poly T to the 3' end of the first cDNA strands with a terminal nucleotide transferase as templates and complementary oligo C, oligo G, oligo T or oligo A as primers.

20. The method of claim 1, wherein the tag molecule has a hydrazine terminus.

21. The method of claim 9, wherein the biotin molecule has a hydrazine terminus.

22. The method of claim 11, wherein the avidin molecule has a hydrazine terminus.

23. A method for making full-length cDNA libraries, which is for making libraries of cDNAs having lengths corresponding to full lengths of respective mRNAs, and comprises the following steps of:

binding a tag molecule to a diol structure present in 5' Cap ($^{7Me}G_{ppp}N$) sites of mRNAs by oxidizing the 5' Cap site diol to form a dialdehyde and reacting the resulting dialdehyde with a tag molecule having a group reactive with the dialdehyde, forming RNA-DNA hybrids by reverse transcription using primers and the mRNAs binding the tag molecule as templates, and separating RNA-DNA hybrids carrying a DNA corresponding to a full-length of mRNA from the RNA-DNA hybrids formed above by using affinity chromatography of the tag molecule.

24. A method for making full-length cDNA libraries, which is for making libraries of cDNAs having lengths corresponding to full lengths of respective mRNAs, and comprises the following steps of:

binding a biotin molecule to a diol structure present in 5' Cap ($^{7Me}G_{ppp}N$) sites of mRNAs by oxidizing the 5' Cap site diol to form a dialdehyde and reacting the resulting dialdehyde with a biotin molecule having a group reactive with the dialdehyde, forming RNA-DNA hybrids by reverse transcription using primers and the mRNAs bound to biotin molecules as templates, digesting the RNA-DNA hybrids with an RNase capable of cleaving single strand RNA to cleave the single strand RNA parts of the hybrids carrying a DNA not corresponding to a full-length mRNA to remove biotin molecules from the hybrids, and separating RNA-DNA hybrids carrying a DNA corresponding to a full-length MRNA and binding the biotin molecules by affinity chromatography to a solid support.

25. A method for making full-length CDNA libraries, which is for making libraries of cDNAs having lengths corresponding to full lengths of respective mRNAs, and comprises the following steps of:

binding an avidin molecule to a diol structure present in 5' Cap ($^{7Me}G_{ppp}N$) sites of mRNAs by oxidizing the 5' Cap site diol to form a dialdehyde and reacting the resulting dialdehyde with an avidin molecule having a group reactive with the dialdehyde, forming RNA-DNA hybrids by reverse transcription using primers and the mRNAs bound to avidin molecules as templates, digesting the RNA-DNA hybrids with an RNase capable of cleaving single strand RNA to cleave the single strand RNA parts of the hybrids carrying a DNA not corresponding to full-length mRNAs to remove avidin molecules from the hybrids, and separating RNA-DNA hybrids carrying a DNA corresponding to a full-length mRNA and binding avidin molecules by affinity chromatography to a solid support.

* * * * *